(12) United States Patent
Krishnan et al.

(10) Patent No.: US 8,040,511 B1
(45) Date of Patent: Oct. 18, 2011

(54) AZIMUTH ANGLE MEASUREMENT

(75) Inventors: Shankar Krishnan, Santa Clara, CA (US); Haixing Zhou, Sunnyvale, CA (US); Haiming Wang, Fremont, CA (US); David Lidsky, San Jose, CA (US); Walter Dean Mieher, Los Gatos, CA (US)

(73) Assignee: KLA-Tencor Corporation, San Jose, CA (US)

( * ) Notice: Subject to any disclaimer, the term of this patent is extended or adjusted under 35 U.S.C. 154(b) by 457 days.

(21) Appl. No.: 12/357,294

(22) Filed: Jan. 21, 2009

Related U.S. Application Data

(60) Provisional application No. 61/024,510, filed on Jan. 29, 2008.

(51) Int. Cl.
*G01J 4/00* (2006.01)
(52) U.S. Cl. ....................................... 356/369
(58) Field of Classification Search .............. 356/369; 250/559.09
See application file for complete search history.

(56) References Cited

U.S. PATENT DOCUMENTS

| | | | | |
|---|---|---|---|---|
| 6,031,614 | A | 2/2000 | Michaelis et al. | 356/369 |
| 6,882,413 | B2 | 4/2005 | Bowman | 356/369 |
| 7,428,060 | B2 * | 9/2008 | Jin et al. | 356/601 |
| 2007/0223011 | A1 * | 9/2007 | Jin et al. | 356/625 |

OTHER PUBLICATIONS

U.S. Appl. No. 61/024,510, filed Jan. 29, 2008 by Shankar Krishnan, et al.
David B. Chenault and Russell A. Chipman, "Measurements of Linear Diattenuation and Linear Retardance Spectra with a Rotating Sample Spectropolarimeter"—Applied Optics, vol. 32(19), pp. 3513-3519, Jul. 1, 1993.
Y. Cui and R.M.A. Azzam, "Applications of the normal-incidence rotating-sample ellipsometer to high- and low-spatial-frequency gratings," Applied Optics, vol. 35(13), pp. 2235-2238, May 1, 1996.
M. I. Alonso, M. Garriga, F. Alsina, and S. Piñol, "Determination of the Dielectric Tensor in Anisotropic Materials" App. Phys. Lett. vol. 67(5), pp. 596-598, Jul. 31, 1995.

* cited by examiner

*Primary Examiner* — Roy Punnoose
(74) *Attorney, Agent, or Firm* — Joshua D. Isenberg; JDI Patent

(57) ABSTRACT

Methods and apparatus for measuring an optical azimuth angle $\phi_O$ of a substrate relative to a plane of detection in scatterometry tools are disclosed. A grating target on a stage of a scatterometry tool may be illuminated and positions of the resulting diffraction orders may be observed. The optical azimuth angle may be determined from the positions of the diffraction orders. Alternatively, polarization-dependent signals of radiation scattered from a line grating may be measured for equal and opposite polarization angles +A and −A. A combination signal may be computed from the polarization-dependent signals obtained at +A and −A and a property of the combination signal may be calculated for several mechanical Azimuth angles $\phi_M$. A relationship between the optical azimuth angle $\phi_O$ and the mechanical azimuth angle $\phi_M$ may be determined from a behavior of the property as a function of mechanical azimuth angle $\phi_M$.

36 Claims, 10 Drawing Sheets

AZIMUTH ANGLE MEASUREMENT

PRIORITY CLAIM

This application claims the benefit of priority of commonly assigned U.S. Provisional Patent Application No. 61/024,510, filed Jan. 29, 2008, the entire disclosures of which are incorporated herein by reference.

FIELD OF THE INVENTION

This invention generally relates to scatterometry and more particularly to calibration of optical azimuth angle in scatterometry.

BACKGROUND OF THE INVENTION

For a number of industrial applications, it is useful to determine the surface metrology of samples such as thickness of thin films, their refractive indices and the profile parameters of surface features such as grating on semiconductor wafers. A number of metrology tools are now available for performing optical measurements on semiconductors. Such tools can include scatterometers, such as spectroscopic reflectometers, angle-resolved reflectometers, and angle-resolved ellipsometers, and spectroscopic ellipsometers. Such scatterometry techniques have been extensively used in semiconductor metrology, e.g., for measuring film thickness.

In doing scatterometry it is common to look at light reflected from a periodic line or three dimensional structures. A theoretical spectrum for scattered light may be calculated based on a theoretical model based on assumptions about the geometry and material nature of the structure and knowledge of physics and optics. This theoretical spectrum may be compared against a measured spectrum obtained through scatterometry measurements. Through an iterative regression, the theoretical spectrum may be varied by varying the assumptions about the geometry and material nature of the structure until the theoretical spectrum matches the measured spectrum. In an alternative implementation, the measured spectrum may be compared to a pre-computed set of theoretical spectra. The theoretical spectrum that most closely matches the measured spectrum may be reported, or it may be used as the initial theoretical spectrum to start interactive regression. Another implementation, interpolation between the pre-calculated theoretical spectra may be used to determine an interpolated theoretical spectrum that most closely matches the measured spectrum. The shape model that corresponds to the theoretical spectrum that most closely matches the measured spectrum is then said to be the shape model that most closely represents the actual shape of the structure that produced the measured spectrum. However, in order to properly model the theoretical spectrum, it is important to have an accurate model of the optical system used to obtain the measurements. The properties include the azimuth angle $\phi$, which may be the angle of the plane of incidence of the probe beam with respect to some reference direction in the plane of the sample, such as the direction of the lines of a grating target. Alternatively, the azimuth angle $\phi$ may be the angle of the plane of detection of the scattered radiation with respect to the reference direction in the plane of the sample. The azimuth angle $\phi$ has most often employed is 90 degrees. However this angle is not perfectly controlled and is not measured. If the theoretical angle of the plane of incidence does not match the actual angle of the plane of incidence, the theoretical spectrum will not match the measured spectrum, resulting in an error in the reported shape.

Scatterometry is often used for inspection and metrology in semiconductor processing. Most materials used in semiconductor processes, e.g., silicon, silicon dioxide ("oxide"), silicon nitride ("nitride"), poly-silicon ("poly"), photoresist are optically isotropic. An optically isotropic material is one for which the optical properties (e.g., refractive index) are not dependent on the direction of propagation of light through the material. Because of this, no particular attempt was made to determine the orientation of the plane of incidence of the incident beam relative to the sample (the so-called optical azimuth angle $\phi_O$) during scatterometry associated with semiconductor metrology.

A few studies have been done concerning the azimuth angles in spectroscopic ellipsometer applications. Most of these studies were related to measurement of anisotropic (birefringent) materials. For instance, in "Measurements of Linear Diattenuation and Linear Retardance Spectra with a Rotating Sample Spectropolarimieter" Appl. Opt. 32(19) 3513-3519 (1993) and "Applications of the Normal-Incidence Dielectric Tensor in Anisotropic Materials" App. Phys. Lett. 67(5), pp 596-598 (1995) an optically anisotropic sample was placed on a rotating stage to enable measuring optical properties of the sample. Y. Cui and R. M. A. Azzam, "Applications of the normal-incidence rotating-sample ellipsometer to high- and low-spatial-frequency gratings," Appl. Opt. 35, 2235-(1996) further described a normal incidence rotating sample ellipsometer for measuring gratings. U.S. Pat. No. 6,031,614 and U.S. Pat. No. 6,882,413 disclosed methods and systems for critical dimension (CD) measurements using rotating sample (rotating stage) spectroscopic ellipsometry. In all of the above-described references, the azimuth angles of the sample were assumed to be known. However, in practice, this is generally not the case.

Previous methods of measuring azimuth angle include imaging the position of scattered radiation into an imaging detector. Examples include acquiring multiple images of the scattered beam from a rough surface at a series of focus steps, using a pattern recognition camera to acquire multiple images of a diffracted beam from a grating at a series of grating stage azimuth angles (different wavelengths at different diffraction angles and image positions). For example, a wafer may be mechanically aligned with respect to optics using a mechanical feature on a chuck or holder/prealigner that is based on images of a target on the wafer. Several images may be taken to determine how much the wafer has rotated relative to some mechanical reference. With a rotating chuck, one can rotate the chuck to align the wafer using an image alignment system. Unfortunately, an image alignment system does not measure the optical azimuth angle $\phi_O$ between the plane of incidence or plane of detection and the x-y stage axes or any feature on the wafer. Such a system probably gets the optical azimuth angle correct to within 1 or 2 degrees and is repeatably to within plus or minus 0.1 to 0.5 degree. Image alignment measurement repeatability, by contrast may be of order 0.001 degree. For scatterometry measurements on isotropic samples this may be sufficient, and is certainly an improvement over relying on the pre-aligner wafer load angle.

Such azimuth measurement techniques may suffer from certain disadvantages. For example, imaging a beam scattered from a rough surface while scanning focus of an oblique incident beam may result in other changes to the path of incident beam. The image of a diffracted beam may be influenced by aberrations of the imaging system that may be difficult to separate from the effects of the grating azimuth or asymmetry. Another disadvantage of the previous azimuth measurement systems is that they cover only the incident beam and cannot take into account the optics on the detection side. This can be especially important since the detection aperture may not be perfectly centered on the incident beam or scattered beam.

It is within this context that embodiments of the present invention arise.

BRIEF DESCRIPTION OF THE DRAWINGS

Other objects and advantages of the invention will become apparent upon reading the following detailed description and upon reference to the accompanying drawings in which.

DESCRIPTION OF THE SPECIFIC EMBODIMENTS

Figure 1A:
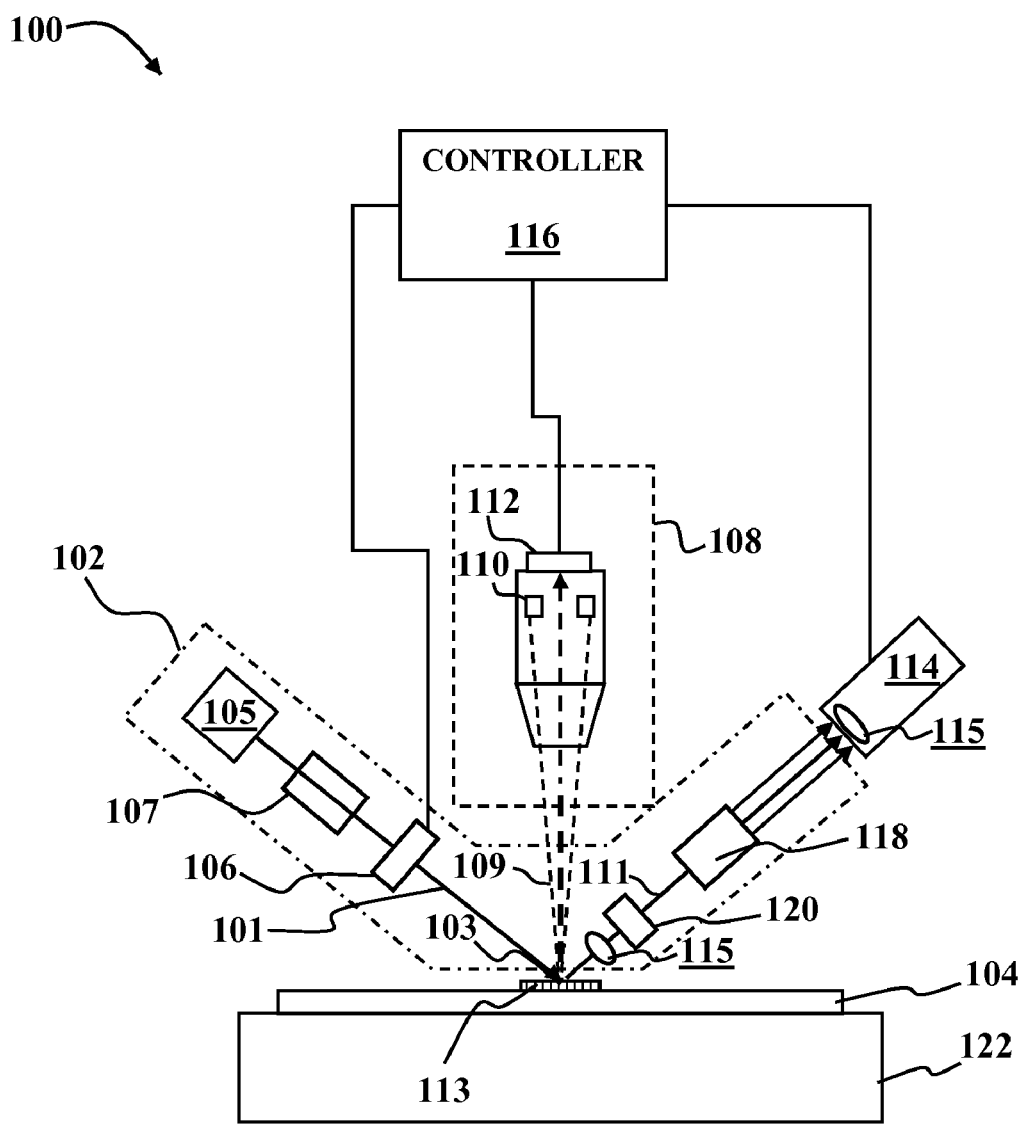
FIG. 1A is a schematic diagram of a spectroscopic ellipsometer of a type that may be used in conjunction with azimuth angle measurement according to an embodiment of the present invention.

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

According to embodiments of the present invention, azimuth angle between a plane of a detected scatterometer beam and a periodic structure that scatters the detected beam may be measured by analyzing properties of the resulting measured scatterometer signal. The error in optical azimuth angle $\phi_O$ may significantly impact the measurement accuracy. For certain samples an optical azimuth angle error $\delta\phi_O$ as small as 0.1 degree may cause the system to fail in meeting tool-to-tool matching specifications.

One type of scatterometry technique, known as spectroscopic ellipsometry, is based on observation of polarization of light from a probe beam that is scattered from a sample. Ellipsometry typically measures two of the four Stokes parameters, which are conventionally denoted by $\Psi$ and $\Delta$. The Stokes parameters are a set of values that describe the polarization state of electromagnetic radiation. The polarization state of the light incident upon the sample may be decomposed into an s and a p component (the s component is oscillating perpendicular to the plane of incidence and parallel to the sample surface, and the p component is oscillating parallel to the plane of incidence). The amplitudes of the s and p components, after scattering and normalized to their initial value, are denoted by $r'_s$ and $r'_p$, respectively. Ellipsometry measures $\rho$ the ratio of $r'_s$ and $r'_p$, which is described by the fundamental equation of ellipsometry:

$$\rho = \frac{r'_p}{r'_s} = \tan(\Psi)e^{i\Delta}$$

Thus, tan $\Psi$ is the amplitude ratio $\rho$ upon reflection, and $\Delta$ is the phase shift. Ellipsometry is an indirect method, i.e. in general the measured values of $\Psi$ and $\Delta$ cannot be converted directly into the optical constants of the sample. Normally, a model analysis must be performed to extract parameters of the sample. Direct inversion of $\Psi$ and $\Delta$ is possible in certain simple cases involving isotropic and homogeneous thick films. In other cases a layer model may be established, which considers the optical constants (e.g., refractive index or dielectric function tensor) and thickness parameters of all individual layers of the sample including the correct layer sequence. Using an iterative procedure (e.g., least-squares minimization) unknown optical constants and/or thickness parameters are varied, and $\Psi$ and $\Delta$ values are calculated using the Fresnel equations. The calculated $\Psi$ and $\Delta$ values, which match the experimental data best, provide the optical constants and thickness parameters of the sample.

Examples of properties that may be derived from standard ellipsometric measurements include, but are not limited to film thicknesses and dielectric function, substrate dielectric function, and, by inference, film stoichiometry. Examples of properties that can be derived from the signal due to modulation of the pump beam include, but are not limited to band structure, band gap, mobility, density of states, strain, dopant concentration and profile, and the like.

FIG. 1A depicts an example of a scatterometer system 100 that may be used in conjunction with optical azimuth angle measurement according to embodiments of the present invention. The system 100 may generally include a scatterometer 102 that is configured to deliver a probe beam 101 to a measurement spot 103 on a sample 104 and to measure one or more ellipsometric parameters of the sample 104 at one or more discrete wavelengths or wavelength ranges or over a range of wavelengths or for a plurality of wavelengths across a wavelength range. By way of example, the scatterometer 102 may include a probe beam radiation source 105 and appropriate optical elements 107 for delivering the probe beam 101 to the measurement spot 103. The path of light from the radiation source 105 to the measurement spot 103 is sometimes referred to herein as the oblique incidence optical path for probe radiation. The relevant wavelength range for the probe beam 101 may vary from material to material depending on the optical properties of the materials and the grating structure.

The scatterometer 102 may be any of several different types of tools including reflectometers and ellipsometers. By way of example, and without loss of generality, the scatterometer 102 may be a spectroscopic ellipsometer 102. An example of a measurement system which includes a spectroscopic ellipsometer is a SpectraFx 200 model tool from KLA-Tencor of San Jose, Calif. In such a case, the scatterometer 102 may include a rotating optical element 106 that is configured to modulate a polarization of the probe beam 101. By way of example, the rotating optical element may be a polarizer, e.g., Nichol prism, or the like in a rotating mount that rotates about an axis parallel to an optical axis of the probe beam 101. Rotation of the optical element 106 modulates the polarization of the probe beam 101. The use of rotating element 106 to modulate the polarization allows for lower frequency modulation of the polarization, e.g. at modulation frequencies ranging from about 1-5 Hz up to about 60 Hz.

In the case where the scatterometer 102 is an ellipsometer, the scatterometer 102 may further include an analyzer element 120 that selects a polarization of signal radiation 111 that is reflected, diffracted, scattered or otherwise emitted from the measurement spot 103 on the sample 104 as a result of interaction between the sample material and the probe beam 101. Additional optical components, e.g., lenses, mirrors, compensator plates, filters and the like, optically couple the signal radiation 111 (or a portion thereof) to a detection system 114, which may be part of the scatterometer 102 or separate from it.

In embodiments of the present invention, the system 100 may include a normal incidence optical column 108 configured to provide illumination of the target with normal incidence radiation and/or allow for imaging of the sample 104 or a portion thereof near to the measurement spot 103. By way of example, the normal-incidence optical column 108 may include an illumination source 110 and an imaging system 112 such as a charge-coupled-device (CCD) camera. By way of example, the imaging system 112 may include a pattern recognition camera. Examples of a pattern recognition camera include cameras made by companies such as Sony, Cohu or Panasonic, combined with frame-grabbing hardware and software developed by Matrox or Cognex. The illumination source 110 may include a broadband source, such as a lamp, or a narrow band source, such as a laser. The imaging system 112 collects light scattered from the sample 104 and generates an image from the collected scattered light. The image may be displayed on a screen or stored in electronic form for analysis. The scattered light that is collected by the imaging system 112 may originate at the illumination source 110 in the normal incidence optical column 108. Alternatively, the imaging system 112 may collect and image scattered light originating from the probe beam radiation source 105.

The normal incidence optical system 108 may be configured to vary a wavelength of normal incident illumination 109 over one or more wavelength ranges. In some embodiments the light source 110 may include a continuum pump light source and a variable filter or monochromator configured to select a particular wavelength or wavelength range for the pump beam 109 from among a range of wavelengths. Alternatively, the light source 110 may be otherwise configured to produce a wavelength-tunable pump beam. For example, the pump light source 110 may include a tunable laser. Examples of suitable tunable lasers include Vibrant model lasers available from Opotek, Inc. of Carlsbad, Calif. Further information about such lasers may be found on the Internet at http://www.opotek.com/vibrant.htm.

As discussed above, the detection system 114 is optically coupled to the scatterometer 102. By way of example, the scatterometer 102 and/or detection system 114 may include collection optics 115 that collect light scattered from or otherwise generated at the measurement spot 103 on the sample 104. The detection system 114 is configured to measure standard ellipsometric signals and/or signals due to effects of the modulated pump beam on one or more sample properties. A controller 116 may be coupled to the detection system 114. The controller 116 may be configured to extract one or more properties of the sample 104 from the standard ellipsometric signals, the parameters derived from the signals due to effects of the modulated pump beam, or both. By way of example, and without limitation, the controller may implement extraction of the properties of the sample by way of code instructions running on a suitable processor. Such instructions may be implemented in hardware, in software or some combination of hardware and software.

The scatterometer 102 may include a spectrometer 118 configured to resolve the standard ellipsometric signals at each of a plurality of wavelengths. By way of example, the spectrometer 118 may be a dispersive spectrometer, comprising prisms, a diffraction gratings, or a combination of diffraction gratings and prisms. Alternatively, the spectrometer 118 may be a Fourier transform spectrometer. Alternatively, the spectrometer 118 may include a monochromator or variable filter configured to sequentially select one or more of the plurality of wavelengths from the probe beam 101.

In embodiments of the present invention, the optical azimuth angle $\phi_O$ may be determined through use of a sample 104 that contains a grating target 113 at or near the measurement spot 103. The grating target 113 generally includes a plurality of parallel regularly spaced linear features. A diffraction grating is a good example of a grating target. Alternatively, electronic circuit features on a semiconductor wafer may have a grating-type structure characterized by linear features that a sufficiently parallel, sufficiently regularly spaced and spaced close enough to each other that they scatter radiation in a manner similar to that of a diffraction grating. Such features may be used as the grating target 113.

The grating target 113 may be a periodic target structure specially built for the purpose of optical azimuth measurement or for optical profile measurement using scatterometry. Alternatively, the grating target may include periodic circuit features on a semiconductor that meet predetermined criteria for spacing between features and symmetry of the features. Preferably, the grating target 113 includes a periodic grating structure characterized by a substantially regular spacing. As used herein, the term "substantially regular spacing" means that a variation in the grating period is small compared to a spot placement reproducibility of the incident beam. It is often desirable for the plane of detection to be perpendicular to grating lines in the grating target 113. The target is illuminated with incident radiation that lies within a "cone" of incidence and detected over a "cone of detection". The incidence cone is typically larger than the detected cone. The reason for this is that a larger incidence cone provides more incident radiation to the target, which provides a better signal and better measurement precision.

In embodiments of the present invention, the sample 104 may be retained by a stage 122. The sample 104 may be mechanically aligned with respect to the stage 122, e.g., using a notch or flat on the sample and a corresponding feature on the stage. The grating features on the grating target 113 may then be mechanically aligned by rotating the stage 122 and sample 104 about a z-axis and observing an image of the grating target 113 with the imaging system 112. A mechanical azimuth angle $\phi_M$ of the grating target may be determined with respect to a coordinate direction of the imaging system 112. By way of example, the mechanical azimuth angle $\phi_M$ may be defined with respect a direction parallel to or perpendicular to parallel lines on the grating target 113. However, the mechanical azimuth angle $\phi_M$ may be different from an optical azimuth angle $\phi_O$ that is defined with respect to a plane of incidence of radiation incident on the grating target 113 or a plane of detection of radiation scattered from the grating target 113.

Figure 1B:
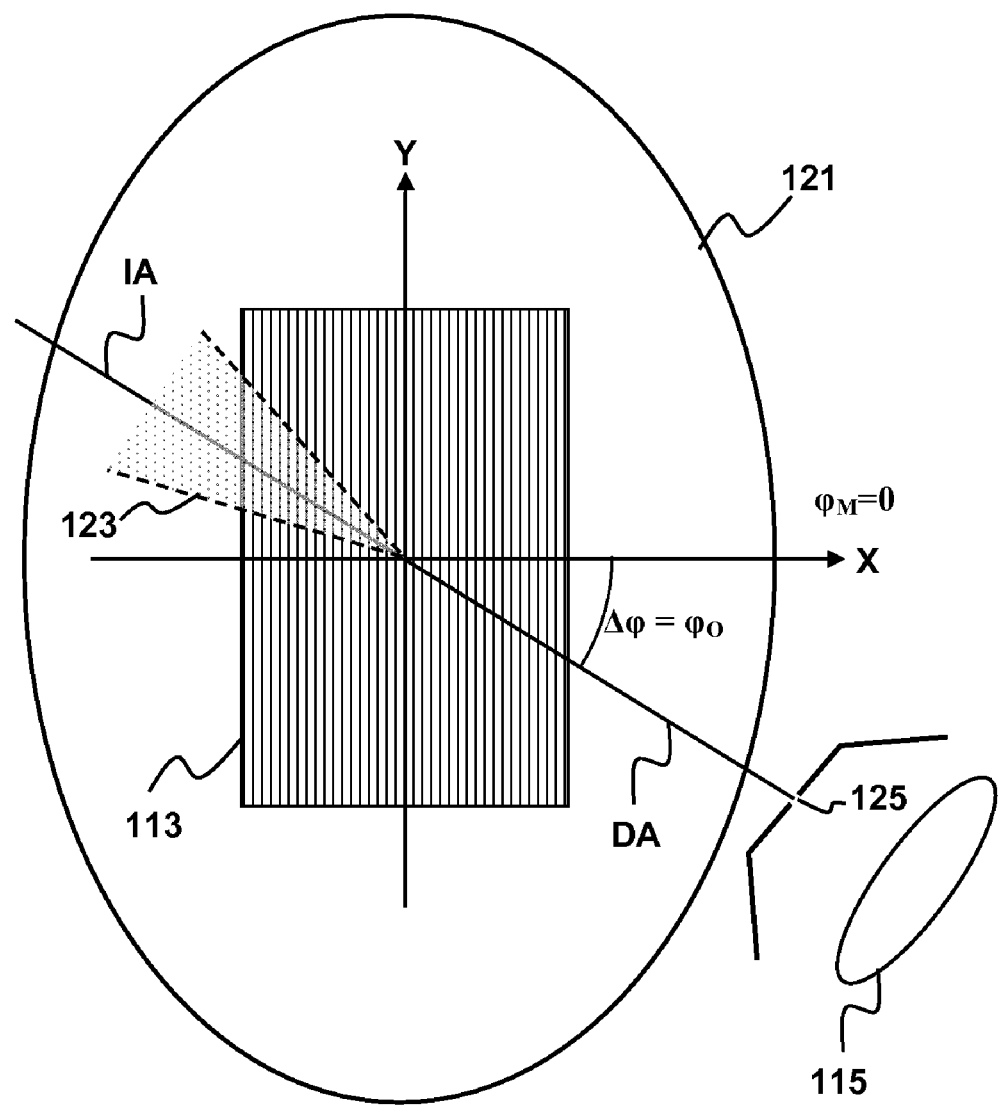
FIG. 1B is a schematic diagram of a grating sample illustrating a coordinate system used in azimuth angle measurement according to an embodiment of the present invention.

The difference between the mechanical azimuth angle $\phi_M$ and the optical azimuth angle $\phi_O$ is shown in FIG. 1B. In practical implementations, the coordinates of the imaging system 112 may be very accurately defined with reference to the stage 122. When the grating target 113 is loaded and placed within a field of view 121 of the imaging system 112, the mechanical azimuth angle $\phi_M$ of structures, such as grating lines, may be measured with respect to camera coordinate directions, X, Y in an image of the target and accurately defined. In a practical scatterometer system, one typically loads the grating sample with a null mechanical azimuth angle as shown in FIG. 1B. In this example, the grating lines of the target 113 are oriented parallel to the Y axis and perpendicular to the X axis. The optical azimuth angle $\phi_O$ may be defined with respect to an incidence plane of the scatterometer system. The incidence plane may be regarded as a plane perpendicular to a plane of the target 113 that contains an axis of a IA cone of radiation 123 illuminating the target 113. Alternatively, the optical azimuth angle $\phi_O$ may be defined with respect to a plane perpendicular to a plane of the target 113 that contains a detection axis DA, which may be defined by an entrance aperture 125 of the collection optics 115. It is noted that the plane of incidence and the plane of detection may be aligned with each other or may be at an angle with respect to each other depending on the design or assembly of the scatterometer. The optical azimuth angle $\phi_O$ is typically close to the mechanical azimuth angle $\phi_M$, but may include a small offset angle $\delta\phi$. Embodiments of the present invention provide a method to accurately calibrate this offset angle $\delta\phi$ and thereby accurately calibrate the optical azimuth angle $\phi_O$. It is noted that in this example a zero value of the optical azimuth angle $\phi_O$ corresponds to a situation in which the plane of incidence and/or plane of detection is oriented perpendicular to line features in the grating target 113. Alternatively, embodiments of the present invention may work where a zero optical azimuth angle is defined for an incidence plane oriented at some other angle to the line features, e.g., where the line features are oriented parallel to the plane of incidence.

Certain embodiments of the present invention may take advantage of the high sensitivity of the positions of these diffraction orders to the azimuth angle as determined by the orientation of the grating lines with respect to the incidence plane or detection plane of the scatterometer 102. In particular, the grating target 113 is illuminated with radiation which is diffracted by the grating target. The resulting diffraction orders are then imaged, e.g., using the imaging system 112. The optical azimuth angle $\phi_O$ may be measured from the position of the diffraction orders in the camera field of view and based on the known geometry of the grating targets. The difference between the mechanical azimuth angle $\phi_M$ and the optical azimuth angle $\phi_O$ may thus be easily determined. To improve calibration accuracy, one may rotate the sample to set the mechanical azimuth angle to certain values and measure the positions of the diffraction orders accordingly. In principle, one may just need to load the sample 104 once. The mechanical azimuth angle $\phi_M$ may be determined by a sample handling system and the stage 122.

By way of example, and without limitation, the correlation between the orientation of the diffraction orders in the field of view 121 may be implemented by code instructions running on a suitable processor coupled to the scatterometer 102. Actuators and sensors may be used to automate rotation of the stage 122 and determination of the mechanical azimuth angle $\phi_M$. Control of the rotation of the stage and measurement of the mechanical azimuth angle $\phi_M$ may be implemented in hardware or software or some combination of hardware and software. The imaging system 112 may generate a digital image of the field of view 121. Digital image analysis may be used to quantify the orientation of the diffraction orders from analysis of the digital image. The digital image analysis may be implemented in hardware, in software or some combination of hardware and software. Appropriately configured software may then correlate the quantified orientation of the diffraction orders to the measured values of the azimuth angle $\phi_M$, determine the offset $\delta\phi$ between $\phi_O$ and $\phi_M$ and take the offset into account in determining the value of $\phi_O$.

Figure 2:
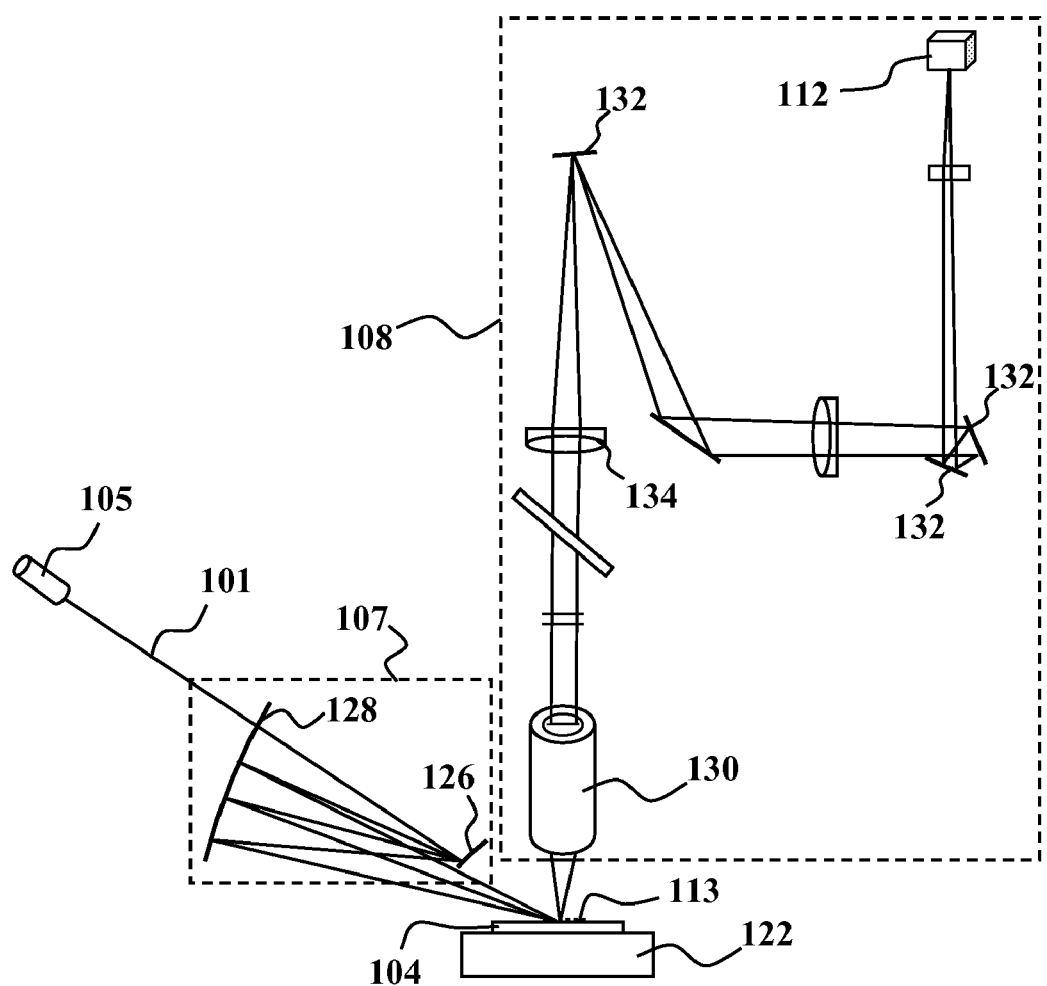
FIG. 2 is a schematic diagram of a portion of a spectroscopic ellipsometer illustrating illumination of a grating sample along a spectroscopic ellipsometer illumination path for azimuth angle measurement according to an embodiment of the present invention.

There are numerous possible configurations for illuminating the grating target 113 and determining the optical azimuth angle $\phi_O$ from the diffraction orders. For example, FIG. 2 schematically depicts a case in which the target 113 is illuminated with radiation from the probe beam radiation source 105. It is noted that the probe beam radiation source 105 may be a monochromatic light source such as a laser diode, or a broadband light source (e.g., a Xenon lamp). In the example depicted in FIG. 2, the sample is illuminated using the spectroscopic ellipsometer illumination path and normal incidence signal collection. The grating target 113 may be illuminated by coupling a broadband light source to the scatterometer's illumination path via an optical fiber. Alternatively a narrow band light source, such as a laser diode, may be coupled to the illumination path. By way of example, a grating target having 800 lines per millimeter may be used for calibrating azimuth angles near zero. Calibration standard gratings may be developed for other azimuth angles, e.g., angles near 45 degrees for certain applications. Gratings with various pitches can be used to modulate the location of the diffracted orders. The radiation 101 is focused onto the target using the optical elements 107 which may include a diffraction grating 126 and a focusing mirror 128. Use of the diffraction grating 126 allows illumination of the grating target 113 with very narrow-band radiation. Incident radiation 101 that is diffracted from the grating target may be imaged through the normal incidence optical column 108 and observed using the imaging system 112. By way of example, the optical column 108 may include an objective lens 130 that collimates the diffracted radiation to form a parallel beam and a series of mirrors 132 and lenses 134 that deflect and focus the diffracted radiation into the imaging system 112. In such a configuration, the optical azimuth angle $\phi_O$ may be determined from the observed locations and orientations of the diffraction orders in the field of view of the imaging system 112 as shown in FIGS. 3A-3C.

Figure 3A:
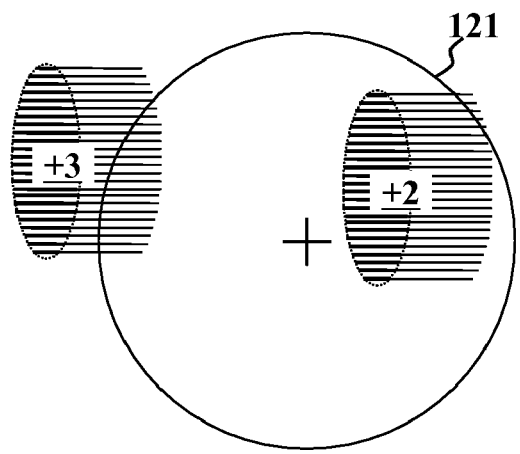
FIGS. 3A-3C are schematic diagrams illustrating diffraction orders viewed in a camera field of view with a grating target at different mechanical azimuth angles $\phi_M$ for illumination of the type shown in FIG. 2.
Figure 3B:
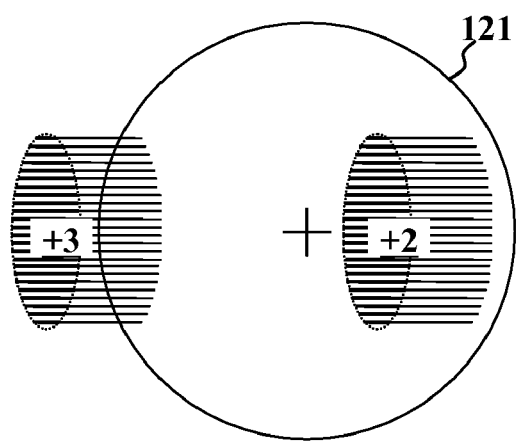
Figure 3C:
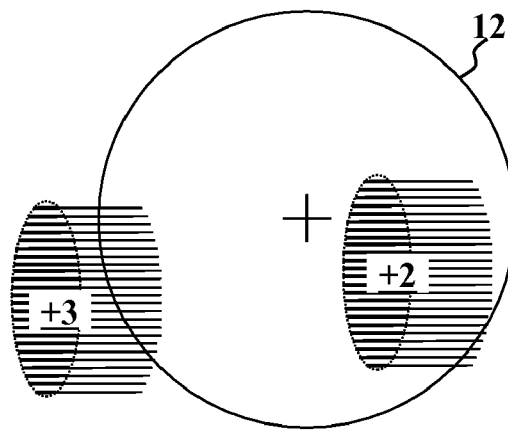

Specifically, FIGS. 3A-3C illustrate certain experiments in which a grating sample with 800 lines per millimeter was used as the grating target 113. The scatterometer used was a Aleris 8500 model manufactured by KLA-Tencor. In this example the +3 diffraction order and the +2 diffraction order are visible in the field of view 121 of the imaging system 112.

The target was illuminated using a laser source that was inserted in the optical path of the ellipsometer.

In this particular experiment, the specular reflection ($0^{th}$ order light) is outside the field of view of the camera system. The $+2^{nd}$ and $+3^{rd}$ diffraction orders fell into the field of view. When the sample was rotated, the positions of these diffraction orders were observed change with respect to the camera field of view, as illustrated in FIGS. 3A-3C. FIG. 3A illustrates the relative positions of the diffraction orders in the field of view 121 when the optical azimuth angle $\phi_O$ is offset from alignment with the plane of incidence (i.e., offset from $\phi_O=0$ in this example) by an amount $+\Delta\phi$. Note that in FIG. 3A, the +3 and +2 diffraction orders are above the center of the field of view 121 indicated by the cross. FIG. 3C illustrates the relative positions of the diffraction orders in the field of view 121 when the optical azimuth angle $\phi_O$ is offset from alignment with the plane of incidence by an equal and opposite amount $-\Delta\phi$. Note that in FIG. 3C, the +3 and +2 diffraction orders are below the center of the field of view 121. FIG. 3B illustrates the relative positions of the diffraction orders in the field of view 121 when the optical azimuth angle $\phi_O$ is aligned with the plane of incidence by an amount ($\phi_O=0$). Note that in FIG. 3B, the +3 and +2 diffraction orders are even with the center of the field of view 121.

Figure 4:
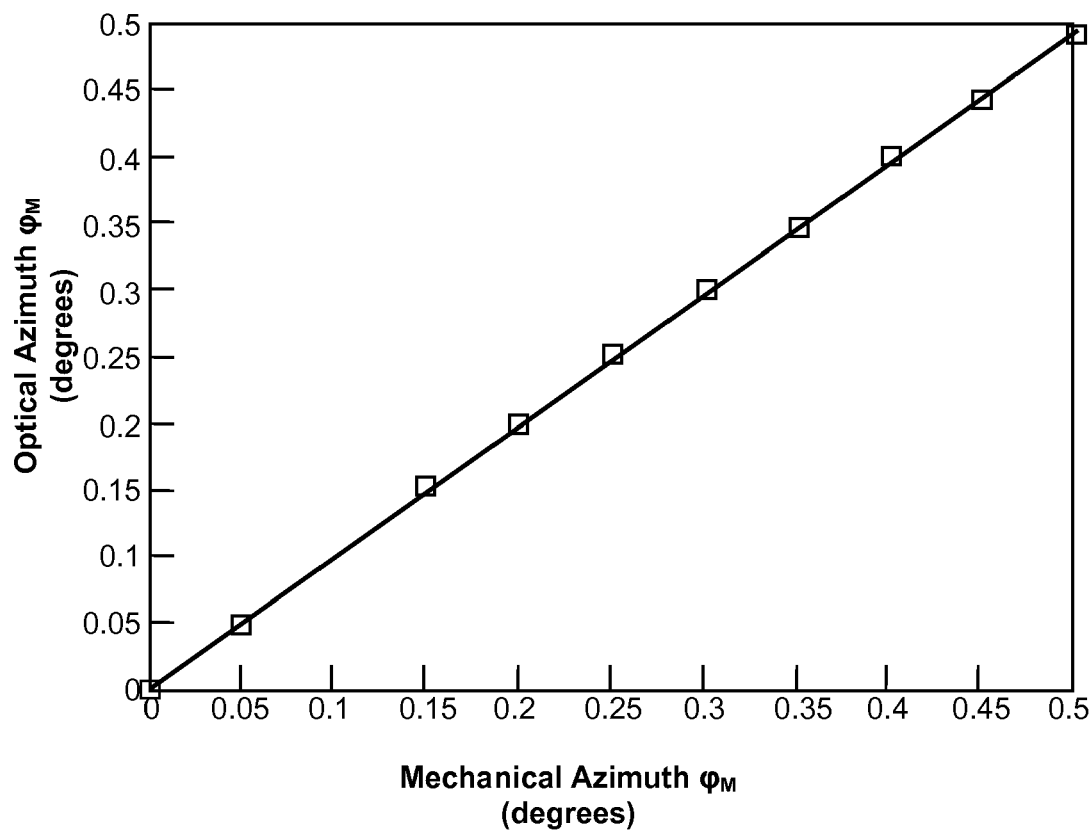
FIG. 4 is a graph of optical azimuth angle $\phi_O$ versus mechanical azimuth angle $\phi_M$ with a system of the type shown in FIG. 1.

As may be seen from FIGS. 3A-3C, by rotating the sample 104 until the diffraction orders are centered and noting the mechanical azimuth angle $\phi_M$ corresponding to this condition one may determine the offset $\delta\phi$ between $\phi_M=0$ and $\phi_O=0$. Furthermore, once the offset $\delta\phi$ has been determined, the positions of the diffraction orders observed in the field of view 121 may be correlated to corresponding optical azimuth angle values. FIG. 4 shows results of optical azimuth angles $\phi_O$ in relation with mechanical azimuth angles $\phi_M$ ranging from zero degrees to 0.5 degrees at a step of 0.05 degrees. In FIG. 4, the offset $\delta\phi$ of the optical azimuth angle $\phi_O$ relative to the mechanical azimuth angle $\phi_M$ has been subtracted out to better illustrate the linear relation between the mechanical azimuth angle $\phi_M$ and the optical azimuth angle $\phi_O$. In this example, the accuracy of the calibration was limited by the stage rotation accuracy.

Alternatively, the optical azimuth of the plane of detection may be similarly calibrated by illuminating the target 113 through the collection optics 115 and observing the resulting diffraction pattern in the field of view of the imaging system 112.

Figure 5:
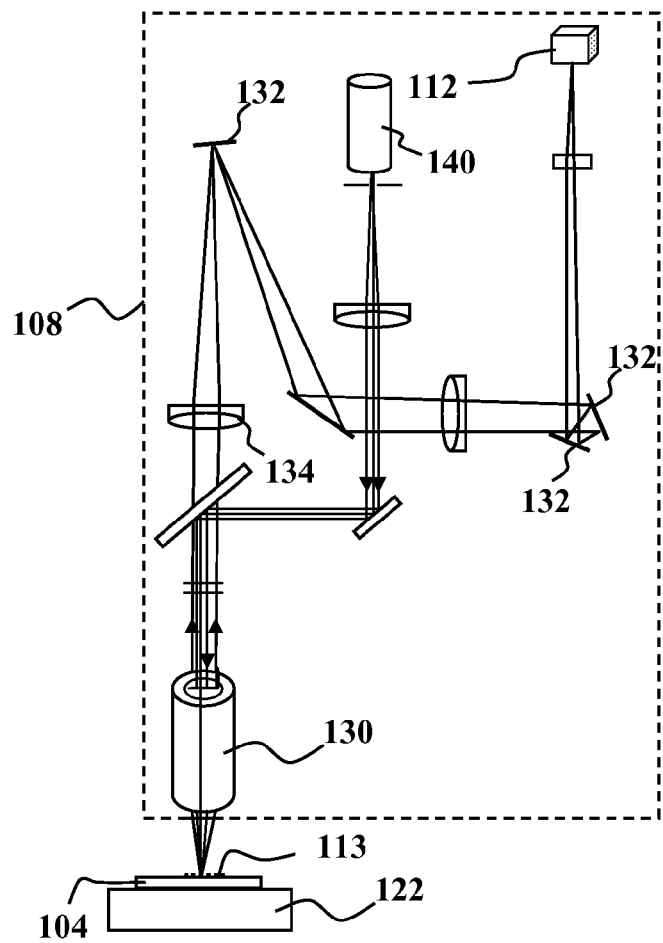
FIG. 5 is a Schematic diagram illustrating an alternative spectroscopic ellipsometer configuration for azimuth angle measurement utilizing illumination of a grating target along a normal incidence path according to an embodiment of the present invention.

In an alternative embodiment, illustrated in FIG. 5 and FIGS. 6A-6C, the illumination light may be launched onto the gating target 113 from the normal direction and the diffraction orders may be observed in the normal direction as well. In this manner, one may pick the images of both specular ($0^{th}$ order) and higher order diffractions. Specifically, as seen in FIG. 5, a radiation from a broadband source 140, e.g., a white light LED beam may be directed onto a grating target 113 at normal incidence. The broadband source 140 may be optically coupled to the objective 130 of the normal incidence optical column 108 through a one or more mirrors 132, lenses 134 and a beam splitter 136. Light diffracted from the target 113 may be coupled to the imaging system 112 through mirrors 132 and lenses 134 as described with respect to FIG. 2.

Figures 6A, 6B, 6C:
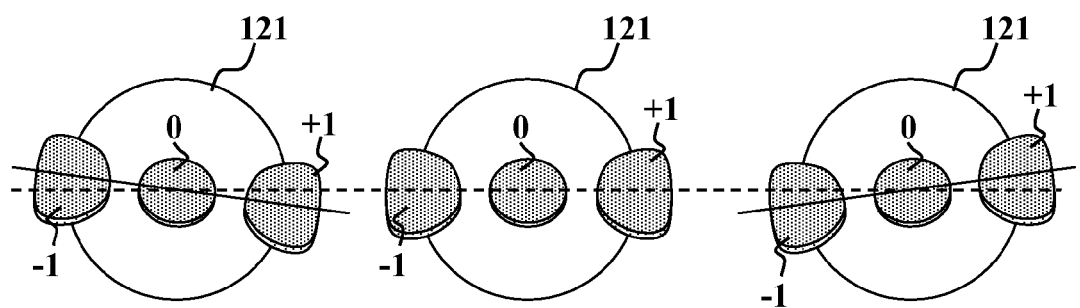
FIGS. 6A-6C are schematic diagrams illustrating diffraction orders viewed in a camera field with a grating target at different mechanical azimuth angles for a system of the type shown in FIG. 5.

As seen from FIGS. 6A-6C, the $0^{th}$ order ((specular reflection)) and +1/−1 diffraction orders may be viewed within a pattern recognition field of view 121 of the imaging system 112. When the target 113 is rotated about the z-axis, the positions of these diffraction orders change accordingly. For example FIG. 6A illustrates the relative positions of the diffraction orders in the field of view 121 when the optical azimuth angle $\phi_O$ is offset from =0 by an amount $+\Delta\phi$. Note that in FIG. 3A, the −1 and +1 diffraction orders are not aligned with the x-axis of the field of view 121. FIG. 3C illustrates the relative positions of the diffraction orders in the field of view 121 when the optical azimuth angle $\phi_O$ is offset from alignment with the plane of incidence by an equal and opposite amount $-\Delta\phi$. In FIG. 3C, the −1 and +1 diffraction orders are also out of alignment with the x-axis of the field of view 121 but in an opposite sense of rotation compared to their positions in FIG. 3A. FIG. 3B illustrates the relative positions of the diffraction orders in the field of view 121 when the optical azimuth angle $\phi_O$ is aligned ($\phi_O=0$). Note that in FIG. 3B, the −1 and +1 diffraction orders are aligned with the x-axis of the field of view 121.

The change in the positions of the diffraction orders may be directly related to corresponding changes in the mechanical azimuth angle $\phi_M$. Furthermore, a reference optical azimuth angle, e.g., zero optical azimuth, may be established and associated with a particular configuration of the positions of the diffraction orders. For example, the configuration of the diffraction orders within the field of view seen in FIG. 6B may be associated with a 0 degree optical azimuth angle. A reference line may be drawn between the centers of the three diffraction orders in the field of view. When the sample is rotated as in FIG. 6A or FIG. 6C, the positions of the diffraction orders change. New reference lines may be drawn between the centers of the diffraction patterns for these cases. The optical azimuth angle may be measured by measuring the angle between the reference line determined from the configuration in FIG. 6B with similar reference lines for the diffraction order configurations in FIG. 6A or FIG. 6C, and correlating these measurements to corresponding mechanical azimuth angles.

Figure 7:
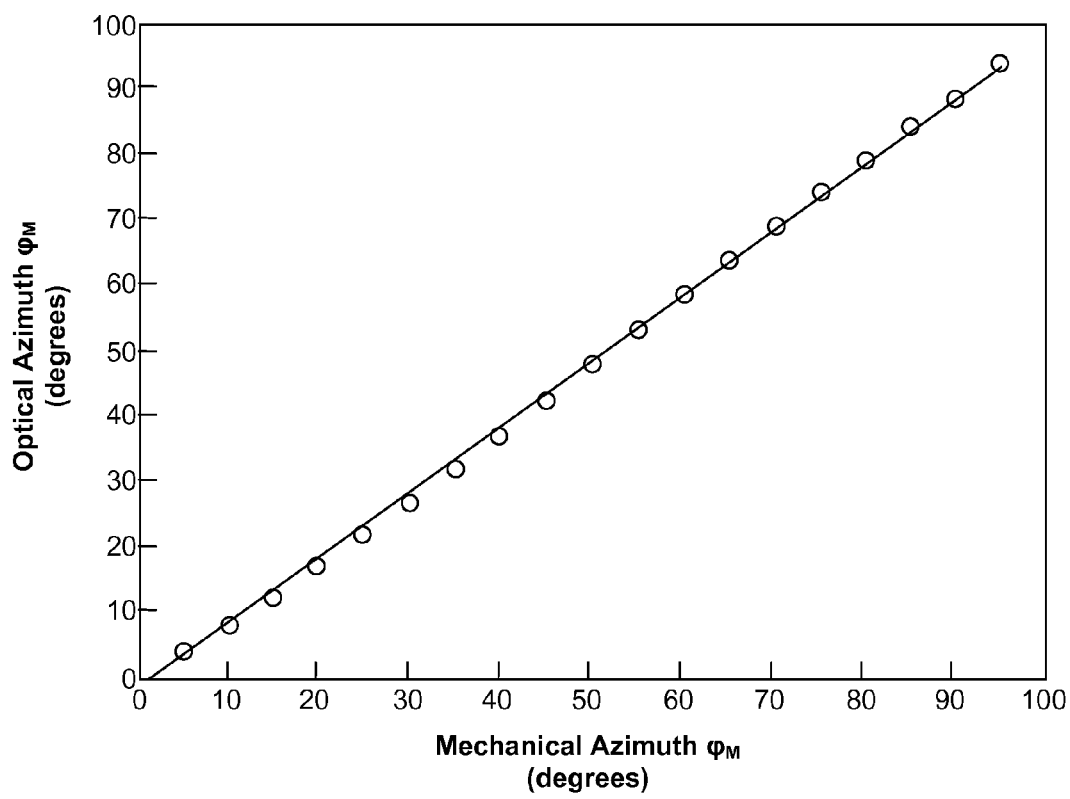
FIG. 7 is a graph of optical azimuth angle versus mechanical azimuth angle with a system of the type shown in FIG. 5.

An example of such measurement results is shown in FIG. 7. In this case, optical azimuth angle was plotted as a function of mechanical azimuth angle (as determined from image orientation) from a range of mechanical azimuth angles from zero to 95 degrees. A grating target having 830 lines/mm was observed using a Alerts 8500 model spectroscopic ellipsometer manufactured by KLA-Tencor.

The difference between this alternative embodiment and embodiments in which the illumination beam is launched from the scatterometer illumination path is that in the embodiment illustrated in FIG. 5, FIGS. 6A-6C and FIG. 7 is that the position of the incidence plane of the pattern recognition optical system is measured instead of the incidence plane of the scatterometer system. However, by combining the two methods, one can calibrate the offset angle between the incidence plane of the pattern recognition system and the scatterometer system. Once this offset angle has been calibrated, this alternative method may be used in real-time to monitor azimuth angles during scatterometry measurements on samples such as semiconductor wafers. Because the illumination used for optical azimuth angle measurement is not launched via the probe beam path of the scatterometer 102, there is little to no potential interaction with the probe beam 101. Second, and more importantly, in this method one may use a single grating sample to cover a wide range of rotation angles, thereby making it possible to measure azimuth angles at real sample gratings with various pitches.

Alternative Embodiments of the present invention are directed to measurement of the Azimuth angle between the plane of a detected ellipsometer beam and a period structure or grating that a detected beam has beam scattered from by analyzing the measured properties of detected ellipsometer signal. Such embodiments of the present invention may take advantage of the fact that certain quantities derived from scatterometry measurements have both a dependence on optical azimuth angle $\phi_O$ and a symmetric or asymmetric behavior with respect to the angle of polarization of the incident or scattered radiation. Certain quantities that may be derived from ellipsometer measurements include a dependence on an analyzer angle A, which may be determined from the angle of the polarization direction of the analyzer element 120, e.g., with respect to a direction parallel to the plane of detection.

Figure 8:
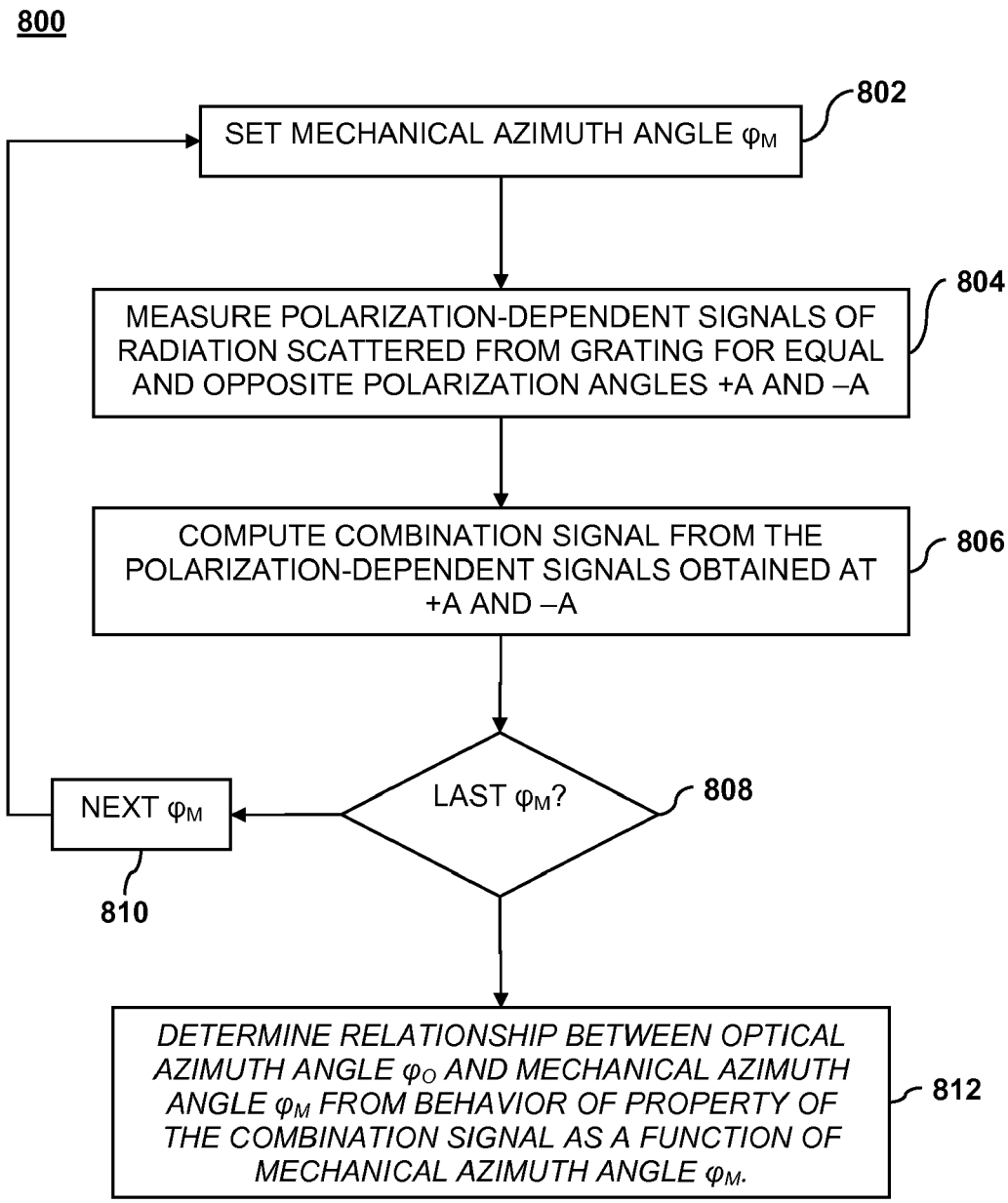
FIG. 8 is a flow diagram illustrating a method for optical azimuth angle measurement according to an alternative embodiment of the present invention.

Certain embodiments of the present invention make use of the fact that for an ellipsometric signal that is asymmetric in a polarization angle and in azimuth angle, there should be combination signal (sum or difference) that is non-zero at non-zero azimuth, but goes to zero or a minimum at optical azimuth $\phi_O=0$. By way of example, a method 800 for optical azimuth angle measurement may proceed as shown in the flow diagram of FIG. 8. By way of example, and without limitation, the method 800 may be implemented, in whole or in part, by means of coded instructions running on a processor within the controller 116. A mechanical azimuth angle for a grating target may be set as indicated at 802. Polarization-dependent signals $S_{+A}$, $S_{-A}$ may then be measured for radiation scattered from the grating target for equal and opposite polarization angles of the scattered radiation +A and −A as indicated at 804. The polarization angle A refers to an angle of the polarization of the scattered radiation with respect to a direction parallel to the plane of detection. It is noted that the polarization-dependent signals may include signal values taken a number of different wavelengths $\lambda_i$ of the incident radiation. The polarization-dependent signals $S_{+A}$, $S_{-A}$ may be based on combinations of the amplitudes of the normalized s and p components of the detected scattered radiation, $r'_s$ and $r'_p$ respectively.

As indicated at 806 a combination signal $S_C$ may be computed from the polarization-dependent signal $S_{+A}$ obtained at +A and the polarization-dependent signal $S_{-A}$ obtained at −A. By way of example, the combination signal $S_C$ may include a difference of $S_{+A}$ and $S_{-A}$ or a sum of $S_{+A}$ and $S_{-A}$ or some other mathematical combination of $S_{+A}$ and $S_{-A}$. This procedure may be repeated for a number of different mechanical azimuth angles $\phi_M$. For example, at 808 if the most recent value of $\phi_M$ was not the last such value, the next value of $\phi_M$ may be used in subsequent iterations.

The nature of the combination signal $S_C$ may depend on factors other than the symmetric or asymmetric nature of the underlying polarization-dependent signal. For example, for a grating target made of symmetric structures, i.e., a symmetric grating, if the plane of detection is equal to the plane of symmetry there should be a zero difference between the signal for alpha (or a similar symmetric quantity derived from scatterometry signals) at minus and plus analyzer angles. If the grating structures are symmetric, the illumination is symmetric and the polarization dependent signals $S_{+A}$, $S_{-A}$ are symmetric then the signals $S_{+A}$, $S_{-A}$ would be expected to be the same when the plane of incidence is parallel to the grating structures on the grating target. If the line elements are not symmetric, the signals $S_{+A}$, $S_{-A}$ would not be expected to be the same. Furthermore, if the grating structures of the target are symmetric, the illumination is symmetric and the polarization dependent signals $S_{+A}$, $S_{-A}$ are symmetric but the ellipsometer optics between the grating target and the detector are not symmetric, the signals $S_{+A}$, $S_{-A}$ would not be expected to be the same.

A property P of the combination signal $S_C$ may then be calculated as indicated at 810. The combination signal $S_C$ may depend on the wavelength of the incident radiation $\lambda_i$. In such a case, it may be desirable to calculate the property P based on values of the combination signal for different wavelengths $\lambda_i$. By way of examples, the property P may be based on an average of values of $S_C$ for different wavelengths $\lambda_i$, or a sum of values of $S_C$ for different wavelengths $\lambda_i$, or an integral of values of $S_C$ over a range of wavelengths $\lambda_i$, or a value of $S_C$ at a particular wavelength $\lambda_i$.

As indicated at 812, a relationship between the optical azimuth angle $\phi_O$ of the plane of detection and the mechanical azimuth angle may then be determined from a behavior of the property P as a function of mechanical azimuth angle $\phi_M$. By way of example, and without limitation, a root mean square (RMS) or $\chi^2$ value may be computed for the combination signal $S_C$ at each mechanical azimuth angle $\phi_M$ and then fit to a parabola to determine a minimum value. Alternatively, the combination signal $S_C$ (keeping the sign) may be fit to a line or polynomial function and an offset between $\phi_O$ and $\phi_M$ may be determined from a zero intercept of the function.

In a particular embodiment, the property P of the combination signal $S_C$ may be an approximately linear function of mechanical azimuth angle $\phi_M$ for a suitably small range of $\phi_M$. In such a case, an offset between the optical azimuth angle $\phi_O$ and the mechanical azimuth angle $\phi_M$ may be determined from a value of the mechanical azimuth angle $\phi_M$ for which the property P is equal to zero. This stage azimuth angle corresponds to a true optical plane of detection or true zero optical azimuth angle $\phi_O=0$. Alternatively, the property of the combination signal may be an approximately quadratic function of mechanical azimuth angle $\phi_M$. In such an offset between the optical azimuth angle $\phi_O$ and the mechanical azimuth angle $\phi_M$ may be determined from a value of the mechanical azimuth angle $\phi_M$ for which the property P has a minimum value.

As noted above, there are numerous possible signals obtained from ellipsometry measurements that may be used as the polarization-dependent signals $S_{+A}$, $S_{-A}$. In addition, there are a number of different possibilities for suitable grating targets. Examples of polarization-dependent signals $S_{+A}$, $S_{-A}$ include, but are not limited to α and β, which are defined as follows:

$$\alpha = \frac{|r'_p \cos A|^2 - |r'_s \sin A|^2}{|r'_p \cos A|^2 + |r'_s \sin A|^2} \quad \text{Equation 1}$$

$$\beta = \frac{2\text{Re}(r'_p \cos A \cdot r'^{*}_s \sin A)}{|r'_p \cos A|^2 + |r'_s \sin A|^2} \quad \text{Equation 2}$$

In Equation 2 the notation "Re" refers to the real part of the quantity in parentheses and the quantity $r'^{*}_s$ refers to the complex conjugate of the amplitude of the s-polarized component $r'_s$ of the detected signal.

As an example, optical azimuth angle may be determined from measurements of α and/or β signals from a line grating target for polarization angles +A and −A at a variety of mechanical azimuth angles $\phi_M$, e.g., from about $+\phi_M=2$ degrees to about $\phi_M=-2$ degrees. In some cases, a larger range of mechanical azimuth angles $\phi_M$ may be used. For example, the mechanical azimuth angle $\phi_M$ may be varied in small steps over a range of, e.g., from −20 degrees to +20 degrees in 2 degree increments. The angular resolution required may be determined with simulations of the signals or signal differences versus azimuth angle.

In these examples it is noted that α is a symmetric quantity with respect to analyzer angle A and β is an asymmetric quantity with respect to analyzer angle A. If the signal is symmetric and the sample is symmetric one would expect the same value of α at analyzer angle +A and analyzer angle −A. It is further noted that it would be expected that β would change sign due to the sin(A) term. If the signal and sample are both symmetric and a different is observed for α at +A and −A one may deduce that the optics on the detection side are asymmetric.

Furthermore, when the azimuth angle of the plane of incidence or detection corresponds to a symmetry point of the sample one would also expect the value of α to be the same at +A and −A. In particular, with grating targets the scattering depends on the optical azimuth angle $\phi_O$ and while r' and r'$_p$ are the same for equal and opposite optical azimuth angles $\pm\phi_O$, when the analyzer angle A is not set to zero, it breaks the symmetry so there is a difference between α(+$\phi_O$, A) and α(−$\phi_O$, A) for non-zero optical azimuth angle $\phi_O$. This difference in α grows with increasing optical azimuth angle $\phi_O$, approximately linearly for small values of the optical azimuth angle $\phi_O$ near $\phi_O$=0. The difference is expected to be zero when the plane of incidence is perpendicular to the line grating. Other optical calibrations may need to be taken into account, especially those involving other asymmetries of the optical system. It is noted that both α and β are generally functions of wavelength $\lambda_i$ of the incident radiation so the measurements of the α and β signals may be measured over some range of wavelengths $\lambda_i$.

Figure 9:
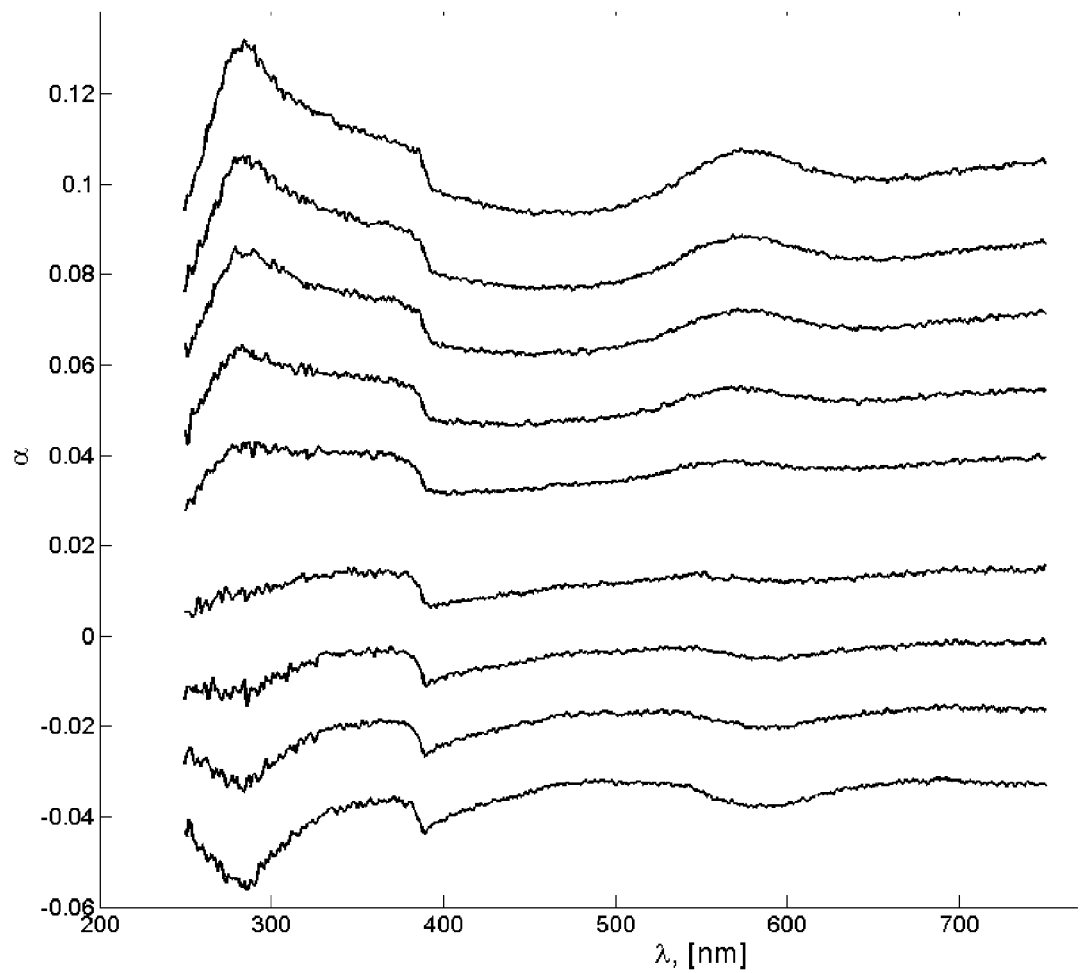
FIG. 9 is a graph depicting Alpha difference spectra for nine different wafer azimuth angles ranging from about −2 degrees to about +2 degrees illustrating optical azimuth angle measurement in spectroscopic ellipsometry in accordance with an alternative embodiment of the present invention.

The α($\phi_M$, +A) signal may be subtracted from the α($\phi_M$, −A) signal at each mechanical azimuth angle $\phi_M$ to obtain a difference signal Δα($\phi_M$, $\lambda_i$). By way of example, FIG. 9 illustrates the results of an experiment in which values of α-difference signals Δα($\phi_M$, $\lambda_i$) for radiation scattered from a grating target were measured with a spectroscopic ellipsometer over a range of incident wavelengths $\lambda_i$ for 9 different mechanical azimuth angles $\phi_M$ from about −2 degrees to +2 degrees.

A property $P_\Delta$ of the difference signal Δα($\phi_M$, $\lambda_i$) may then be calculated. Examples of properties of Δα($\phi_M$, $\lambda_i$) include, but are not limited to an integral of Δα($\phi_M$) over a wavelength range, an average of Δα($\phi_M$, $\lambda_i$) over a wavelength range, a sum of Δα($\phi_M$) over a wavelength range, a value of Δα($\phi_M$, $\lambda_i$) at a specific wavelength, etc. It is desirable to compute a property $P_\Delta$ in a way that uses information from signals obtained over a range of wavelengths. In a preferred embodiment, the difference signal Δα($\phi_M$, $\lambda_i$) is an approximately linear function of mechanical azimuth angle $\phi_M$ for a small range of $\phi_M$ (e.g., a few degrees). The value of $\phi_M$ where the difference signal Δα($\phi_M$, $\lambda_i$) goes to zero may be regarded as azimuth angle for the true optical plane of detection or true $\phi_O$=0. The X-intercept of a linear fit of a property $P_\Delta$ of the difference signal Δα($\phi_M$, $\lambda_i$) (Y-axis) as a function of mechanical azimuth $\phi$ (X-axis) gives the value of the azimuth where the detected spectroscopic ellipsometer beam is perpendicular to the grating lines.

A similar technique may be used for the β signal, except that a sum signal:

$$\tau\beta(\phi_M,\lambda_i)=\beta(\phi_M,\lambda_i,+A)+\beta(\phi_M,\lambda_i,-A)$$

is calculated instead of a difference signal due to β being asymmetric in analyzer angle while α is symmetric.

Figure 10:
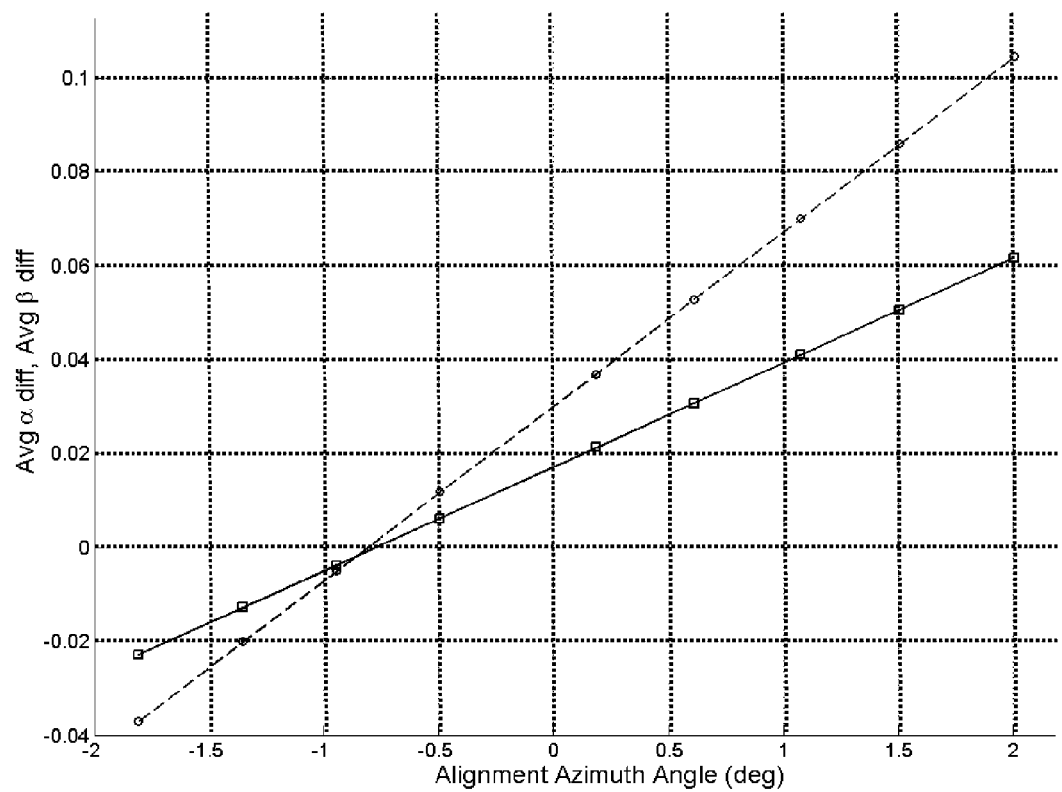
FIG. 10 is a graph showing plots and linear fits of α-difference average spectra and β-sum average spectra versus azimuth angle illustrating azimuth angle measurement in spectroscopic ellipsometry in accordance with an alternative embodiment of the invention.

FIG. 10 depicts a graph containing plots and linear fits of the averages of α-difference spectra (dashed line) and β-sum spectra (solid line) obtained from a grating target versus mechanical Azimuth angle $\phi_M$. The X-intercept of the two linear fits indicate the value of the mechanical Azimuth angle $\phi_M$ for which the detected scattered ellipsometer beam is perpendicular to the grating lines of the target. The X-intercepts will most likely be different for the α-difference spectra and β-sum spectra if there are any uncorrected or uncalibrated asymmetries in the optical system. A weighted average, $\phi_{avg}\alpha\beta$, may be calculated between the $\phi_M(\Delta\alpha=0)$ and $\phi_M(\Delta\beta=0)$, with weighting factors that may include signal to noise ratios, accuracy of the $\phi_{avg}\alpha\beta$ result, robustness of the $\phi_{avg}\alpha\beta$ result. An alternative approach is to calculate the optical azimuth $\phi_O$ at each incident wavelength $\lambda_i$, and then calculate a weighted average optical Azimuth $\phi_{O\text{-}avg}$ based on azimuth sensitivity and noise. It is noted that the result obtained may generally depend on details of the algorithm, including wavelength range, wavelength weighting, grating target measured, calibrations applied, etc.

It has been observed that the intercepts for α-difference and β-sum plots tend to agree for small pitch targets (e.g., grating spacing less than about 300 nanometers) but tend to diverge for larger grating spacings. It is therefore desirable in some embodiments to use a grating target 113 having a grating period of less than about 300 nanometers. This corresponds to a grating with greater than about 3,333 lines per mm.

Embodiments of the present invention allow for measurement of the optical azimuth angle $\phi_O$ of a detected ellipsometer beam using symmetry principles. Measurement of optical azimuth angle in accordance with embodiments of the invention does not require modeling of the measured spectrum or matching of modeled spectra to measured spectra. In the particular case where the combination signal is linear with respect to mechanical azimuth angle $\phi_M$ detection of the symmetry condition (zero crossing) may be easier than detection of a maxima or minima on a quadratic signal. Embodiments of the invention have demonstrated a result uncertainty of less than 5 millidegrees, which is much better than previous techniques.

Embodiments of the present invention may be all varieties of ellipsometers. Furthermore, the polarization dependent signals $S_{+A}$, $S_{-A}$ may be generalized to include a full range of Mueller Matrix information and different kinds of ellipsometer signals. Although examples of optical azimuth measurement have been described and demonstrated using a linear grating target, optical azimuth measurement may alternatively be performed on two-dimensional periodic structures. With future development it should be possible to extract more information about the asymmetry of the detected ellipsometer beam and potentially map the aperture function at each wavelength.

In embodiments of the present invention, the measured optical azimuth angle $\phi_O$ may be used in a number of different ways. For example, $\phi_O$ may be used to determine a required rotation of the wafer or wafer holder or wafer rotation stage to bring $\phi_O$ to a required optical azimuth angle or within a permissible range of the required optical azimuth angle. In other embodiments, $\phi_O$ may be used to determine the required rotation of the optical system to bring $\phi_O$ to the required optical azimuth angle or within a permissible range of the required optical azimuth angle. The measured value of the optical azimuth angle $\phi_O$ may also be used to determine a required adjustment of one or more optical components of the scatterometer system 100 to bring $\phi_O$ to the required optical azimuth angle or within a permissible range of the required optical azimuth angle. In other embodiments, $\phi_O$ is used as system calibration parameter for the scatterometer system 100, e.g., a system optics calibration parameter, or a system rotation stage calibration parameter.

In some embodiments, the measured value of the optical azimuth angle $\phi_O$ may be used in calculating one or more theoretical scattering signals or spectra. Such theoretical spectra may be compared to one or more measured signal spectra. In the case of a grating target 113, a result of a comparison between measured and theoretical spectra may be used, e.g., for the purpose of determining a structure of the grating elements that make up the target 113.

In other embodiments, the measured value of the optical azimuth angle $\phi_O$ may be used in calculating and applying a correction, approximate correction, or modification of one or more theoretical or measured scattering signals or spectra. Such corrections, approximate corrections or modifications may be applied for the purpose of comparing measured and theoretical spectra.

Optical azimuth measurement results obtained in accordance with embodiments of the present invention may be used to determine the correction necessary to reduce the optical azimuth angle to meet specifications. The optical azimuth angle result may be used as a calibration value or correction factor in OCD scatterometry signal analysis to improve accuracy and tool matching.

Future developments to improve OCD sensitivity and extend OCD technology to smaller feature sizes may increasingly rely on azimuth accuracy. Azimuth angle error is a significant part of the OCD scatterometry tool matching differences and resulting accuracy errors. Measuring, reducing, calibrating and correcting for this azimuth error will enable OCD systems to meet tighter tool matching requirements and accuracy specifications.

While this description discusses examples of a method and apparatus used on a semiconductor wafer, the method and apparatus are general and may be applied to any other workpiece, including, but not limited to, a photolithographic mask, a flat panel display, a photo-voltaic solar panel, a magnetic data storage component, or a micro-mechanical device component. Furthermore, although certain examples are described in terms of particular ellipsometer architectures, embodiments of the invention are not limited to such architectures. Instead, the method described herein may also be applied to other fixed polarizer, rotating analyzer ellipsometer systems including Mueller matrix ellipsometers, laser based ellipsometers, and the like.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A method for measuring an optical azimuth angle $\phi_O$ of a substrate relative to a plane of incidence or a plane of detection in a scatterometry tool, comprising:
   a) illuminating a grating target on a sample with incident light directed along an optical path through the scatterometry tool;
   b) generating an image containing two or more diffraction orders of the incident light that is diffracted from the grating target with an imaging system;
   c) measuring an orientation of the two or more diffraction orders relative to a coordinate system of the imaging system; and
   d) correlating the orientation of the two or more diffraction orders relative to the coordinate system to a value of the optical azimuth angle $\phi_O$ of the grating target relative to the plane of incidence or the plane of detection of the scatterometry tool.

2. The method of claim 1 wherein d) includes: rotating the grating target with respect to a z-axis until the orientation of the two or more diffraction orders corresponds to a known orientation for the diffraction orders at a zero value of the optical azimuth angle $\phi_O$; measuring a mechanical azimuth angle $\phi_M$ of the grating target relative to a mechanical reference on the scatterometry tool that corresponds to the zero value of the optical azimuth angle $\phi_O$ and determining an offset $\delta\phi$ between the mechanical azimuth angle $\phi_M$ and the zero value of the optical azimuth angle $\phi$.

3. The method of claim 2, wherein d) further includes measuring the orientation of the diffraction orders at a plurality of different measured mechanical azimuth angles, correlating each measured orientation of the diffraction orders to a corresponding mechanical azimuth angle and subtracting out the offset $\delta\phi$ from each measured mechanical azimuth angle $\phi_M$ to determine a corresponding optical azimuth angle $\phi_O$ for each orientation of the diffraction orders that has been measured.

4. The method of claim 1 wherein a) includes illuminating the grating target along an illumination path that is oblique relative to a normal to the grating target, wherein the illumination path coincides with an oblique incidence optical path for probe radiation in the scatterometry tool.

5. The method of claim 1 wherein a) includes illuminating the grating target along an illumination path that is normal to the grating target, wherein the illumination path is different from an oblique incidence optical path for probe radiation in the scatterometry tool.

6. The method of claim 5, further comprising, directing probe radiation to the sample along the oblique incidence optical path and performing scatterometry measurements with the scatterometry tool while performing a), b), c) and d).

7. The method of claim 1, wherein the scatterometry tool is a reflectometer.

8. The method of claim 1, wherein the scatterometry tool is an ellipsometer.

9. The method of claim 8, wherein the ellipsometer is a spectroscopic ellipsometer.

10. The method of claim 1, wherein b) includes illuminating the target through collection optics of the scatterometry tool and observing a resulting diffraction pattern in a field of view of the imaging system.

11. An apparatus for measuring an optical azimuth angle $\phi_O$ of a substrate relative to a plane of incidence or a plane of detection in a scatterometry tool, comprising:
   means for illuminating a grating target with incident light directed along an optical path through the scatterometry tool;
   means for generating an image containing two or more diffraction orders of the incident light that is diffracted from a grating target with an imaging system;
   means for measuring an orientation of the two or more diffraction orders relative to a coordinate system of the imaging system;
   means for correlating the orientation of the two or more diffraction orders relative to the coordinate system to a value of the optical azimuth angle $\phi_O$ of the grating target relative to the plane of incidence or the plane of detection of the scatterometry tool.

12. A method for measuring an optical azimuth angle $\phi_O$ of a substrate relative to a plane of detection in an ellipsometer, comprising:

a) illuminating a grating target on a stage of the ellipsometer with incident radiation;

b) measuring a polarization-dependent signals of incident radiation scattered from a grating target for equal and opposite analyzer angles of the scattered radiation +A and −A, where A is an angle of the polarization of the scattered radiation after it passes through a polarization analyzer with respect to a direction parallel to the plane of detection;

c) computing a combination signal from the polarization-dependent signals obtained at +A and the polarization spectra obtained at −A;

d) calculating a property of the combination signal;

e) repeating a), b), c) and d) for a plurality of mechanical Azimuth angles $\phi_M$ of the grating target relative to the plane of detection; and e) determining a relationship between the optical azimuth angle $\phi_O$ of the plane of detection and the mechanical azimuth angle $\phi_M$ from a behavior of the property of the combination signal as a function of mechanical azimuth angle $\phi_M$.

13. The method of claim 12 wherein the property uses information over a range of wavelengths of the combination signal.

14. The method of claim 12 wherein the property is an integral of the combination signal over a wavelength range, an average of the combination signal over a wavelength range, a sum of the combination signal over a wavelength range or a value of the combination signal at a specific wavelength or set of wavelengths.

15. The method of claim 12 wherein the property of the combination signal is approximately a linear or polynomial function of stage angle.

16. The method of claim 15, further comprising determining a value of the mechanical azimuth angle $\phi_M$ for which a value of the property of the combination signal is zero, and utilizing the value of the mechanical azimuth angle $\phi_M$ for which the value of the property of the combination signal is zero as a zero value for the optical azimuth angle $\phi_O$.

17. The method of claim 12 wherein the polarization-dependent signal includes a plurality of values of a quantity α obtained for different wavelengths of the incident radiation scattered from the grating target, wherein the quantity α is defined as:

$$\alpha = \frac{|r'_p \cos A|^2 - |r'_s \sin A|^2}{|r'_p \cos A|^2 + |r'_s \sin A|^2},$$

wherein $r'_p$ and $r'_s$ are amplitudes of s and p components of the radiation scattered from the grating target normalized to their initial values.

18. The method of claim 17, wherein the combination signal includes a difference between values of α at analyzer angles +A and −A.

19. The method of claim 12 wherein the polarization-dependent signals includes a plurality of values of a quantity β obtained for different wavelengths of the incident radiation scattered from the grating target, wherein the quantity β is defined as:

$$\beta = \frac{2\text{Re}(r'_p \cos A \cdot r'^*_s \sin A)}{|r'_p \cos A|^2 + |r'_s \sin A|^2},$$

wherein $r'_p$ is an amplitude of a p-polarized component of the radiation scattered from the grating target normalized to an initial value, wherein the notation "Re" refers to a real part of $(r'_p \cos A \cdot r'^*_s \sin A)$ and the quantity $r'^*_s$ is a complex conjugate of an amplitude of the s-polarized component $r'_s$ of the detected signal.

20. The method of claim 19, wherein the combination signal includes a sum of the values of β at analyzer angles +A and −A.

21. The method of claim 12 wherein the property of the combination signal is approximately a quadratic function of stage angle.

22. The method of claim 21, further comprising determining a value of the mechanical azimuth angle $\phi_M$ for which the property of the combination signal has a minimum value, and utilizing the stage azimuth angle $\phi_M$ for which the property of the combination signal has the minimum value as a zero value for the optical azimuth angle $\phi_O$.

23. The method of claim 12, further comprising using the measured value of the optical azimuth angle $\phi_O$ to determine a required rotation of the wafer or a wafer holder or a wafer rotation stage to bring $\phi_O$ to a required optical azimuth angle or within a permissible range of the required optical azimuth angle.

24. The method of claim 12, further comprising using the measured value of the optical azimuth angle $\phi_O$ to determine a required rotation of an optical system to bring $\phi_O$ to a required optical azimuth angle or within a permissible range of the required optical azimuth angle.

25. The method of claim 12, further comprising using the measured value of the optical azimuth angle $\phi_O$ to determine a required rotation of the optical system to bring $\phi_O$ to a required optical azimuth angle or within a permissible range of the required optical azimuth angle.

26. The method of claim 12, further comprising using the measured value of the optical azimuth angle $\phi_O$ to determine the required adjustment of one or more optical components to bring $\phi_O$ to a required optical azimuth angle or within a permissible range of the required optical azimuth angle.

27. The method of claim 12, further comprising using the measured value of the optical azimuth angle $\phi_O$ as a system calibration parameter.

28. The method of claim 12, further comprising using the measured value of the optical azimuth angle $\phi_O$ as system optics calibration parameter.

29. The method of claim 12, further comprising using the measured value of the optical azimuth angle $\phi_O$ as a system rotation stage calibration parameter.

30. The method of claim 12, further comprising using the measured value of the optical azimuth angle $\phi_O$ to calculate one or more theoretical scattering signals or spectra.

31. The method of claim 12, further comprising using the measured value of the optical azimuth angle $\phi_O$ to calculate one or more theoretical scattering signals or spectra and comparing the one or more theoretical scattering signals to one or more measured signals or spectra.

32. The method of claim 12, further comprising using the measured value of the optical azimuth angle $\phi_O$ to calculate one or more theoretical scattering signals or spectra, performing a comparison between the one or more theoretical scattering signals to one or more measured signals or spectra and determining a structure of the grating target from a result of the comparison.

33. The method of claim 12, further comprising using the measured value of the optical azimuth angle $\phi_O$ in calculating and applying a correction, approximate correction, or modification of one or more theoretical scattering signals or spectra.

34. The method of claim 12, further comprising using the measured value of the optical azimuth angle $\phi_O$ in calculating and applying a correction, approximate correction, or modification to one or more theoretical scattering signals or spectra for comparison to one or more measured signals or spectra.

35. The method of claim 12, further comprising using the measured value of the optical azimuth angle $\phi_O$ in calculating and applying a correction, approximate correction, or modification of one or more measured scattering signals or spectra.

36. An apparatus for measuring an optical azimuth angle $\phi_O$ of a substrate relative to a plane of detection in an ellipsometer, comprising:
  a) means for illuminating a grating target on a stage of the ellipsometer with incident radiation;
  b) means for measuring a polarization-dependent signals of incident radiation scattered from a grating target for equal and opposite polarization angles of the scattered radiation +A and −A, where A is an angle of the polarization of the scattered radiation with respect to a direction parallel to the plane of detection;
  c) means for computing a combination signal from the polarization-dependent signals obtained at +A and the polarization spectra obtained at −A;
  d) means for calculating a property of the combination signal;
  e) repeating a), b), c) and d) for a plurality of mechanical Azimuth angles $\phi_M$ of the grating target relative to the plane of detection; and
  e) means for determining a relationship between the optical azimuth angle $\phi_O$ of the plane of detection and the mechanical azimuth angle $\phi_M$ from a behavior of the property of the combination signal as a function of mechanical azimuth angle $\phi_M$.

* * * * *